United States Patent
Minatelli et al.

(10) Patent No.: US 9,597,300 B2
(45) Date of Patent: *Mar. 21, 2017

(54) COMPOSITION AND METHOD TO ALLEVIATE JOINT PAIN USING A MIXTURE OF FISH OIL AND FISH OIL DERIVED, CHOLINE BASED, PHOSPHOLIPID BOUND FATTY ACID MIXTURE INCLUDING POLYUNSATURATED EPA AND DHA

(71) Applicant: U.S. NUTRACEUTICALS, LLC, Eustis, FL (US)

(72) Inventors: John A. Minatelli, Mounta Dora, FL (US); W. Stephen Hill, Ocala, FL (US); Rudi E. Moerck, Sanford, FL (US)

(73) Assignee: U.S. NUTRACEUTICALS, LLC, Eustis, FL (US)

( * ) Notice: Subject to any disclaimer, the term of this patent is extended or adjusted under 35 U.S.C. 154(b) by 27 days.

This patent is subject to a terminal disclaimer.

(21) Appl. No.: 14/700,510

(22) Filed: Apr. 30, 2015

(65) Prior Publication Data
US 2015/0231089 A1  Aug. 20, 2015

Related U.S. Application Data

(60) Division of application No. 14/168,031, filed on Jan. 30, 2014, now Pat. No. 9,050,364, which is a continuation of application No. 14/018,593, filed on Sep. 5, 2013, now Pat. No. 9,028,814, which is a continuation of application No. 13/079,238, filed on Apr. 4, 2011, now Pat. No. 8,557,275, which is a continuation-in-part of application No. 12/840,372, filed on Jul. 21, 2010, now Pat. No. 8,481,072.

(60) Provisional application No. 61/227,872, filed on Jul. 23, 2009, provisional application No. 61/345,652, filed on May 18, 2010.

(51) Int. Cl.
| | | |
|---|---|---|
| A61K 31/122 | (2006.01) | |
| A61K 31/202 | (2006.01) | |
| A61K 31/685 | (2006.01) | |
| A61K 31/728 | (2006.01) | |

(52) U.S. Cl.
CPC .......... *A61K 31/122* (2013.01); *A61K 31/202* (2013.01); *A61K 31/685* (2013.01); *A61K 31/728* (2013.01)

(58) Field of Classification Search
CPC .................................................. A61K 31/122
See application file for complete search history.

(56) References Cited

U.S. PATENT DOCUMENTS

| | | |
|---|---|---|
| 4,801,539 A | 1/1989 | Akasaka et al. |
| 5,527,533 A | 6/1996 | Tso et al. |
| 6,476,005 B1 | 11/2002 | Petito et al. |
| 6,800,299 B1 | 10/2004 | Beaudoin et al. |
| 7,078,040 B2 | 7/2006 | Andersson et al. |
| 7,241,463 B2 | 7/2007 | Nielsen |
| 7,247,752 B2 | 7/2007 | Lockwood et al. |
| 8,481,072 B2 | 7/2013 | Minatelli et al. |
| 8,507,757 B2 | 8/2013 | Minatelli et al. |
| 8,524,980 B2 | 9/2013 | Minatelli et al. |
| 9,028,814 B2 | 5/2015 | Minatelli et al. |
| 2003/0091652 A1 | 5/2003 | Ishaq |
| 2003/0096794 A1 | 5/2003 | Niehoff |
| 2004/0180025 A1 | 9/2004 | Long et al. |
| 2004/0180851 A1 | 9/2004 | Long et al. |
| 2004/0234587 A1 | 11/2004 | Sampalis |
| 2004/0241249 A1 | 12/2004 | Sampalis |
| 2006/0078625 A1 | 4/2006 | Rockway |
| 2007/0098808 A1 | 5/2007 | Sampalis |
| 2007/0196894 A1 | 8/2007 | Sim et al. |
| 2007/0270376 A1 | 11/2007 | Chandler |
| 2008/0014282 A1 | 1/2008 | Long et al. |
| 2008/0038780 A1 | 2/2008 | Stocks et al. |
| 2008/0166779 A1 | 7/2008 | Thomas et al. |
| 2009/0061067 A1 | 3/2009 | Tilseth et al. |
| 2009/0170808 A1 | 7/2009 | Ling et al. |
| 2009/0181114 A1 | 7/2009 | Minatelli et al. |
| 2009/0181127 A1 | 7/2009 | Minatelli et al. |
| 2009/0258081 A1 | 10/2009 | Minatelli et al. |
| 2010/0143571 A1 | 6/2010 | Breivik |
| 2010/0291053 A1 | 11/2010 | Clayton et al. |

(Continued)

FOREIGN PATENT DOCUMENTS

| | | |
|---|---|---|
| CN | 102746947 | 10/2012 |
| EP | 1724357 | 11/2006 |

(Continued)

OTHER PUBLICATIONS

Spiller et al., "Safety of an Astaxanthin-Rich Haematococcus Pluvialis Algal Extract: A Randomized Clinical Trial," Journal of Medicinal Food, vol. 6, No. 1, 2003, pp. 51-56.

Capelli et al., "Astaxanthin—Natural Astaxanthin: King of the Carotenoids," Published by Cyanotech Corporation, 2008, pp. 1-148.

Khanafari et al., "Extraction of Astaxanthin Esters From Shrimp Waste by Chemical and Microbial Methods," Iran. J. Environ. Health. Sci. Eng., 2007, vol. 4, No. 2, pp. 93-98.

Deutsch, "Evaluation of the Effect of Neptune Krill Oil on Chronic Inflammation and Arthritic Symptoms," Journal of the American College of Nutrition, vol. 26, No. 1, pp. 39-47 (2007).

Bunea et al., "Evaluation of the Effects of Neptune Krill Oil on the Clinical Course of Hyperlipidemia," Alternative Medicine Review, vol. 9, No. 4, pp. 420-428 (2004).

(Continued)

*Primary Examiner* — Bin Shen
(74) *Attorney, Agent, or Firm* — Allen, Dyer, Doppelt, Milbrath & Gilchrist, P.A.

(57) ABSTRACT

Beneficial and synergistic effects for alleviating joint pain and symptoms of osteoarthritis and/or rheumatoid arthritis have been found using a mixture of fish oil and fish oil derived, choline based, phospholipid bound fatty acid mixture including polyunsaturated EPA and DHA either alone or in combination with other active constituents, including astaxanthin and polymeric hyaluronic acid or sodium hyaluronate (hyaluronan) in an oral dosage form.

10 Claims, No Drawings

(56) References Cited

U.S. PATENT DOCUMENTS

| | | |
|---|---|---|
| 2011/0117207 A1 | 5/2011 | Minatelli et al. |
| 2011/0195061 A1 | 8/2011 | Minatelli et al. |
| 2011/0268811 A1 | 11/2011 | Minatelli et al. |
| 2013/0059768 A1 | 3/2013 | Hallaraker et al. |
| 2014/0005267 A1 | 1/2014 | Minatelli et al. |
| 2014/0023634 A1 | 1/2014 | Minatelli et al. |
| 2014/0148405 A1 | 5/2014 | Minatelli et al. |

FOREIGN PATENT DOCUMENTS

| | | |
|---|---|---|
| EP | 0601698 | 6/2015 |
| GB | 2 103 088 | 2/1983 |
| IN | 201526 | 2/2007 |
| JP | 2005521629 | 7/2005 |
| WO | 03/027267 | 4/2003 |
| WO | 2004/080388 | 9/2004 |
| WO | 2004/112776 | 12/2004 |
| WO | 2011/062953 | 5/2011 |
| WO | 2013/032333 | 3/2013 |
| WO | 2014/013335 | 1/2014 |
| WO | 2014/014766 | 1/2014 |

OTHER PUBLICATIONS

Lee et al., "Astaxanthin Inhibits Nitric Oxide Production and Inflammatory Gene Expression by Suppressing IkB Kinase-Dependent NF-kB Activation," Molecules and Cells, Jun. 2003, vol. 16, No. 1, pp. 97-105.

Ohgami et al., "Effects of Astaxanthin on Lipopolysaccharide-Induced Inflammation In Vitro and In Vivo," Investigative Opthalmology & Visual Science, Jun. 2003, vol. 44, No. 6, pp. 2694-2701.

Mummert et al., "Synthesis and Surface Expression of Hyaluronan by Dendritic Cells and Its Potential Role in Antigen Presentation," Journal of Immunology, 2002, pp. 4322-4331.

Termeer et al., "Hyaluronan—Magic Glue for the Regulation of the Immune Response?" Trends in Immunology, vol. 24, No. 3, Mar. 2003, pp. 112-114.

McKee et al., "Hyaluronan Fragments Induced Nitric-Oxide Synthase in Murine Macrophages Through a Nuclear Factor kB-Dependent Mechanism," Journal of Biological Chemistry, vol. 272, No. 12, Mar. 21, 1997, pp. 8013-8018.

Brown et al., "Turnover of Hyaluronan in Synovial Joints: Elimination of Labelled Hyaluronan from the Knee Joint of the Rabbit," Experimental Physiology, 1991, No. 76, pp. 125-134.

Serhan et al., "Resolution of Inflammation: State of the Art, Definitions and Terms," The FASEB Journal, vol. 21, Feb. 2007, pp. 325-332.Serhan et al., "Resolution of Inflammation: State of the Art, Definitions and Terms," The FASEB Journal, vol. 21, Feb. 2007, pp. 325-332.

Moreland, "Intra-Articular Hyaluronan (Hyaluronic Acid) and Hylans for the Treatment of Osteoarthritis: Mechanisms of Action," University of Alabama at Birmingham, Arthritis Research & Therapy, vol. 5, No. 2, Jan. 2003, pp. 54-67.

Lee et al., "Hyaluronan: A Multifunctional, MegaDalton, Stealth Molecule," Current Opinion in Cell Biology, 2000, pp. 581-586.

Kalman et al., "Effect of a Natural Extract of Chicken Combs with a High Content of Hyaluronic Acid (Hyal-Joint®) on Pain Relief and Quality of Life in Subjects with Knee Osteoarthritis: A Pilot Randomized Double-Blind Placebo-Controlled Trial," Nutrition Journal, Jan. 2008, pp. 1-9.

Necas et al., "Hyaluronic Acid (Hyaluronan): A Review," Veterinarni Medicina, vol. 53, 2008, pp. 397-411.

Nishimoto et al., "Effect of Chondroitin Sulfate and Hyaluronic Acid on Gene Expression in a Three-Dimensional Culture of Chondrocytes," Journal of Bioscience and Bioengineering, vol. 100, No. 1, 2005, pp. 123-126.

Yamawaki et al., "Hyaluronan Receptors Involved in Cytokine Induction in Monocytes," Glycobiology, vol. 19, No. 1, 2009, pp. 83-92.

Lee et al., "Production of Astaxanthin by Haematococcus," Chemicals from Microalgae, Ed: Zvi Cohen, Taylor and Francis, UK (1999), pp. 173-195.

Bjerkeng et al., "Bioavailability of all-E-astaxanthin and Z-isomers of Astaxanthin in Rainbow Trout (*Oncorhynchus mykiss*)," Aquaculture, vol. 157, Issues 1-2, Nov. 1997, pp. 63-82; Abstract Only (2 pages).

Yang et al., "Glioma-Associated Hyaluronan Induces Apoptosis in Dendritic Cells via Inducible Nitric Oxide Synthase: Implications for the use of Dendritic Cells for Therapy of Gliomas," Cancer Res.; May 2002; 62(9):2583-91; Abstract Only (2 pages).

Ghosh et al., "Potential Mechanism of Action of Intra-Articular Hyaluronan Therapy in Osteoarthritis: Are the Effects Molecular Weight Dependent?" Semin Arthritis Rheum.; Aug. 2002; 32(1):10-37; Abstract Only (2 pages).

Rooney et al., "Angiogenic Oligosaccharides of Hyaluronan Enhance the Production of Collagens by Endothelial Cells," Journal of Cell Science; May 1993; 105(Pt 1):213 218; Abstract Only (1 page).

Ruff et al., "Eggshell Membrane in the Treatment of Pain and Stiffness from Osteoarthritis of the Knee: A Randomized, Multicenter, Double-blind, Placebo Controlled Clinical Study," Clinical Rheumatology, Aug. 2009; 28(8):907 14; Abstract Only (1 page).

Schiedt et al., "Natural Occurence of Enantiomeric and Meso-Astaxanthin, 5. Ex Wild Salmon (*Salmo salar* and *Oncorhynchus*)," Helv. Chem. Acta; 1981; 64(2):449-57; Abstract Only (1 page).

Jiang et al., "Hyaluronan in Tissue Injury and Repair," Annu Rev Cell Dev Biology; 2007; 23:435-61; Abstract Only (1 page).

Noble, "Hyaluronan and its Catabolic Products in Tissue Injury and Repair," Matrix Biology; Jan. 2002; 21(1):25-9; Abstract Only (1 page).

Stern et al., "Hyaluronan Fragments: An Information-Rich System," European Journal of Cell Biology; Aug. 2006; 85(8):699-715; Abstract Only (1 page).

Calder, "Polyunsaturated Fatty Acids and Inflammation: Therapeutic Potential in Rheumatoid Arthritis," Current Rheumatology Review 2009, vol. 5, No. 4, Nov. 2009, pp. 214-225.

Calder, "Joint Nutrition Society and Irish Nutrition and Dietetic Institute Symposium on Nutrition and Autoimmune Disease PUFA, Inflammatory Processes and Rheumatoid Arthritis," Proceedings of the Nutrition Society, vol. 67, No. 4, Nov. 2008, pp. 409-418.

Hurst et al., "Dietary Fatty Acids and Arthritis," Prostaglandins, Leukotrienes and Essential Fatty Acids, vol. 82, No. 4-6, Apr. 2010, pp. 315-318.

Sales et al., "Fish Oil Supplementation in Rheumatoid Arthritis," Reumatismo, vol. 60, No. 3, Jul. 2008, pp. 174-179.

Kikuchi et al., "Bibliographical Investigation of Complementary Alternative Medicines for Osteoarthritis and Rheumatoid Arthritis," Geriatrics and Gerontology International, vol. 9, No. 1, 2009, pp. 29-40.

Ruff et al., "Eggshell Membrane: A Possible New Natural Therapeutic for Joint and Connective Tissue Disorders. Results from Two Open-Label Human Clinical Studies," Clinical Interventions in Aging 2009 LNKD-PUBMED: 19554094, vol. 4, May 2009, pp. 235-240.

Ierna et al., "Supplementation of Diet with Krill Oil Protects Against Experimental Pheumatoid Arthritis," BMC Musculoskeletal Disorders 2010 LNKD-PUBMED: 20587038, vol. 11, 2010, 11 pages.

Tou et al., "Krill for Human Consumption: Nutritional Value and Potential Health Benefits," Nutrition Reviews, vol. 65. No. 2, Feb. 2007, pp. 63-77.

Mendes-Pinto et al., "Evaluation of Different Cell Disruption Processes on Encrysted Cells of Haematococcus Pluvialis: Effects on Astaxanthin Recovery and Implications for Bio-Availability," Journal of Applied Phycology, vol. 13, No. 1, Feb. 2001, pp. 19-24.

Nobre et al., "Supercritical Carbon Dioxide Extraction of Astaxanthin and Other Carotenoids from the Microalga *Haematoccus pluvialis*," European Food Research and Technology, vol. 223, No. 6, Mar. 2006, pp. 787-790.

Valderrama et al., "Extraction of Astaxantine and Phycocyanine from Microalgae with Supercritical Carbon Dioxide," Journal of Chemical and Engineering Data, vol. 48, No. 4, Jul. 2003, pp. 827-830.

(56) References Cited

OTHER PUBLICATIONS

Mendes et al., "Applications of Supercritical CO2 Extraction to Microalgae and Plants," Journal of Chemical Technology and Biotechnology, vol. 62, No. 1, Jan. 1995, pp. 53-59.
Krill Oil Monograph, Alternative Medicine Review, vol. 15, No. 1, Apr. 2010, http://www.thorne.com/altmedrev/.fulltext/15/1/84.pdf, pp. 84-86.
Samplalis et al. "Evaluation of the effects of Neptune krill oil on the management of premenstrual syndrome and dysmenorrhea" Alternative Medicine Review, 2003, 8(2): 171-179.
Guerin et al. "Haematococcus astaxanthin: applications for human health and nutrition", Trends in Biotechnology, 2003, 21(5): 210-216.
Hubbard et al. "Lippid extraction from wheat flour using supercritical fluid extraction", Cereal Chem., 2004, 81(6): 693-698.
Nir et al. "BioAslin helps relieve pain and improves performance in patients with rheumatoid arthritis", Health Research and Studies Center, Los Altos, CA, Study Report, May 3, 2002, 8 pgs.
Balogh et al., Absorbstion, uptake and tissue affinity of high-molecular-weight hyaluronan after oral administration in rats and dogs, Journal of Agricultural and Food Chemistry, Oct. 28, 2008, pp. 10582-10593.
Gotoh et al. "Effects of the molecular weight of hyaluronis acid and its action mechanisms on experimental joint pain in rats" Annal of the Rheumatic Diseases, 19936, 52:817-822.
Bergin et al. "Oral hyaluronan gel reduces post operative tarsocrual effusion in teh yearling thoroughbred", Equine Vetinary j. 2006, 38(4):375-378.
Peer et al. "Tumor-targeted hyaluronan nanoliposomes increase the antitumor activity of liposomal doxorubicin in syngeneic and human xenograft mouse tumor models", Neoplasia, 2004, 6(4):343-353.
Maharjan et al., "High and Low Molecular Weight Hyaluronic Acid Differentially Regulate Human Fibrocyte Differentiation," PLoS ONE, Oct. 2011, vol. 6, Issue 10, pp. 1-10.
Barnett et al., "Treatment of rheumatoid arthritis with oral type II collagen", Arthritis & Rheumatism, vol. 41, No. 2, Feb. 1998, pp. 290-297.
Zavan et al., "Hyaluronan based porous nano-particles enriched with growth factors for the treatment of ulcers: a placebo-controlled study", J. Mater Sci: Mater Med, 2009, pp. 235-244.
Deutsch, "Evaluation of the Effect of Neptune Krill Oil on Chronic Inflammation and Arthritic Symptoms," Journal of the American College of Nutrition, vol. 26, No. 1, Feb. 2007, pp. 39-48.
Nuno et al., "Effects of the Marine Microalgae *Isochrysis galbana* and *Nannochloropsis oculata* in Diabetic Rats," Journal of Functional Foods, vol. 5, No. 1, Jan. 2013, pp. 106-115.
Hurst et al., "Dietary Fatty Acids and Arthritis," Prostaglandins, Leukotrienes and Essential Fatty Acids, vol. 82, No. 4-6, Apr. 1, 2010, pp. 315-318.
Ierna et al., "Supplementation of Diet With Krill Oil Protects Against Experimental Rheumatoid Arthritis," BMC Musculoskeletal Disorders, Biomed Central Ltd., vol. 11, No. 1, Jun. 29, 2010, 11 pages.
Ruff et al., "Eggshell Membrane in the Treatment of Pain and Stiffness from Osteoarthritis of the Knee: A Randomized, Multicenter, Double-blind, Placebo Controlled Clinical Study," Clinical Rheumatology; Journal of the International League of Associations for Rheumatology; vol. 28, No. 8; Apr. 2009; pp. 907-914.
Ruff et al., "Eggshell Membrane: A Possible New Natural Therapeutic for Joint and Connective Tissue Disorders. Results from Two Open-Label Human Clinical Studies," Clinical Interventions in Aging 2009; vol. 4, May 2009, pp. 235-240.

COMPOSITION AND METHOD TO ALLEVIATE JOINT PAIN USING A MIXTURE OF FISH OIL AND FISH OIL DERIVED, CHOLINE BASED, PHOSPHOLIPID BOUND FATTY ACID MIXTURE INCLUDING POLYUNSATURATED EPA AND DHA

RELATED APPLICATION(S)

This is a divisional application of Ser. No. 14/168,031 filed Jan. 30, 2014 (U.S. Pat. No. 9,050,364), which is a continuation application of Ser. No. 14/018,593 filed Sep. 5, 2013 (now U.S. Pat. No. 9,028,814), which is a continuation application of Ser. No. 13/079,238 filed Apr. 4, 2011 (now U.S. Pat. No. 8,557,275), which is a continuation-in-part application of Ser. No. 12/840,372 filed Jul. 21, 2010 (now U.S. Pat. No. 8,481,072), which is based on provisional application Ser. No. 61/227,872, filed Jul. 23, 2009; and provisional application Ser. No. 61/345,652, filed May 18, 2010, the disclosures which are hereby incorporated by reference in their entirety.

FIELD OF THE INVENTION

This invention relates to treating and alleviating symptoms of osteoarthritis and/or rheumatoid arthritis using therapeutic compositions and methods derived from a mixture of fish oil and fish oil derived, choline based, phospholipid bound fatty acids including polyunsaturated EPA and DHA either alone or admixed with synergistic additives.

BACKGROUND OF THE INVENTION

The '372 parent application identified above is directed to the advantageous use of krill oil such as disclosed in U.S. Patent Publication Nos. 2004/0234587; 2004/0241249; and 2007/0098808, the disclosures which are hereby incorporated by reference in their entirety. The beneficial and therapeutic advantages of krill oil are discussed in the various research endeavors that are mentioned in the Background of the Invention section of the '372 application. Such an example is a krill oil manufactured by Neptune Technologies in which a daily dose of about 300 mg reduces arthritic symptoms within a short treatment period of about 7 to 14 days as determined by standard WOMAC scoring procedures.

The '372 application later describes the beneficial and synergistic effects for alleviating joint pain and symptoms of osteoarthritis and/or rheumatoid arthritis when krill oil is used in combination with other active constituents. It has now been found advantageous to use other oils containing certain phospholipid bound polyunsaturated fatty acids not derived from krill in combination with fish oil.

SUMMARY OF THE INVENTION

In accordance with a non-limiting example, even more beneficial and synergistic effects for alleviating joint pain and symptoms of osteoarthritis and/or rheumatoid arthritis have been found when of a mixture of fish oil and fish oil derived, choline based, phospholipid bound fatty acids including polyunsaturated EPA and DHA is used in combination with other active constituents.

In accordance with a non-limiting example, the method treats and alleviates symptoms of osteoarthritis and/or rheumatoid arthritis in a patient by administering a therapeutic amount of a composition including a mixture of fish oil and a fish oil derived, choline based, phospholipid bound fatty acids including polyunsaturated EPA and DHA in combination with astaxanthin and low molecular weight polymers of hyaluronic acid or sodium hyaluronate (hyaluronan) in an oral dosage form.

The mixture of fish oil and fish oil derived, choline based, phospholipid bound fatty acids including polyunsaturated EPA and DHA in one example comprises Eicosapentaenoic (EPA) and Docosahexaenoic (DHA) fatty acids in the form of both triacylglycerides and diacylphospholipids. In one example, the mixture of fish oil and fish oil derived, choline based, phospholipid bound fatty acids including polyunsaturated EPA and DHA comprises not less than 15 g/100 g of fish derived phospholipids, not less than 12 g/100 g of DHA, and not less than 7 g/100 g of EPA. In another example, the mixture of fish oil and fish oil derived, choline based, phospholipid bound fatty acids including polyunsaturated EPA and DHA comprises not less than 22 g/100 g of omega-3 and no less than 3 g/100 g of omega-S. The mixture of fish oil and fish oil derived, choline based, phospholipid bound fatty acids including polyunsaturated EPA and DHA can be further concentrated by supercritical fluid solvent extraction of fish oil triacylglycerides from the choline based phospholipids to decrease fish oil triacylglycerides and increase fish oil derived phospholipids.

In another example, the mixture of fish oil and fish oil derived, choline based, phospholipid bound fatty acids including polyunsaturated EPA and DHA includes at least 15% EPA and 9% DHA, of which not less than 45% are in the form of phospholipids. The composition can be delivered advantageously for therapeutic results with 1-4000 mg of a mixture of fish oil and fish oil derived, choline based, phospholipid bound fatty acids including polyunsaturated EPA and DHA delivered per daily dose. In another example, 0.1-50 mg astaxanthin are added to the mixture of fish oil and fish oil derived, choline based, phospholipid bound fatty acids including polyunsaturated EPA and DHA per daily dose. In one example, the phospholipids comprise 30% or less of the composition.

The astaxanthin is preferably derived from *Haematococcus pluvialis* algae, *Pfaffia*, krill, or by synthetic routes, in the free diol, monoester or diester form or any mixture thereof. The hyaluronic acid or sodium hyaluronate (hyaluronan) can be derived from microbial fermentation or animal tissues. About 1-500 mg of hyaluronan can be delivered per daily dose. In a preferred example, the hyaluronic acid is derived from a biofermenation process and has a surprisingly low molecular weight between 0.5 and 100 kilodaltons (kDa). In another example, the polymers of hyaluronic acid or sodium hyaluronate (hyaluronan) are derived from animal tissue and have molecular weights far exceeding 100 kDa. Such high molecular weight hyaluronans are typically derived from rooster combs and are reportedly mildly anti-inflammatory though this fact is somewhat controversial. The literature clearly indicates that as the molecular weight of hyaluronic acid and its salts increases, its immunogenicity drops dramatically. In addition, more recent scientific literature suggests that low molecular weight hyaluronic acids fragments are unexpectedly highly pro-inflammatory with respect to the innate immune system and would thus not be expected to be useful in the treatment of inflammatory disease states and in particular joint pain associated with OA and/or RH.

The composition may also include a natural or synthetic cyclooxygenase-1 or -2 inhibitor comprising aspirin, acetaminophen, steroids, prednisone, or NSAIDs. The composition may also include a gamma-linoleic acid rich oil comprising Borage (*Borago officinalis* L.) or Safflower (*Carthamus tinctorius* L.).

The composition may also include an n-3 (omega-3) fatty acid rich oil derived from fish oil (EPA and DHA), algae oil (EPA and DHA), flax seed oil (ALA), perilla seed oil (ALA) or Chia seed oil (ALA) and the n-3 fatty acid comprises, either alone or in combination, alpha-linolenic, stearidonic, eicosapentaenoic or docosapentaenoic acid. Soluble or insoluble forms of collagen and elastin such as those derived from hydrolyzed or un-hydrolyzed eggshell membrane can also be advantageously added. The composition may also include anti-inflammatory and/or joint health promoting compounds comprising at least one of the preparations of the green lipped mussel (*Perna canaliculus*), *Boswellia serrata*, turmeric (*Curcuma longer*), stinging nettle (*Urtica dioica*), Andrographis, Cat's claw (*Uncaria tomentosa*), bromelain, methylsulfonylmethane (MSM), chondroitin sulfate, glucosamine hydrochloride or glucosamine sulfate, s-adenosylmethionine, proanthocyanidins, or flavonoids, and preparations of hydrolyzed or un-hydrolyzed eggshell membrane. The composition may include naturally-derived and/or synthetic antioxidants that are added to retard degradation of polyunsaturated fatty acids such as a tocopherol, tocotrienol, carnosic acid or carnisol or mixtures thereof either with or without the potent anti-oxidant astaxanthin.

Different compositions may use different ingredients in combination with the mixture of fish oil and fish oil derived, choline based, phospholipid bound fatty acids including polyunsaturated EPA and DHA, astaxanthin and hyaluronate and be combined with different ingredients and supplemental ingredients for more specific purposes.

A pharmaceutically acceptable composition comprises a mixture of fish oil and fish oil derived, choline based, phospholipid bound fatty acids including polyunsaturated EPA and DHA in combination with astaxanthin and hyaluronate and optionally combined with glucosamine sulfate or its hydrochloride salt, chondroitin sulfate, hydrolyzed or unhydrolyzed collagen, elastin methylsulfonmethane, a gamma-linoleic acid or omega-3 fatty acid rich oil or a cyclooxgenase or lipoxygenase inhibitor for the treatment of symptoms related to joint pain or joint diseases including but not limited to osteoarthritis and rheumatoid arthritis.

In yet another example, a dietary supplement acceptable composition comprises mixture of fish oil and a fish oil derived, choline based, phospholipid bound fatty acid mixture including polyunsaturated EPA and DHA in combination with astaxanthin and hyaluronate and optionally combined with glucosamine sulfate or its hydrochloride salt, chondroitin sulfate, hydrolyzed or unhydrolyzed collagen, elastin methylsulfonmethane, a gamma-linoleic acid or omega-3 fatty acid rich oil and a cyclooxgenase and/or lipoxygenase inhibitor for the treatment of symptoms related to joint pain or joint diseases including but not limited to osteoarthritis and rheumatoid arthritis.

In yet another example, a medical food acceptable composition comprises a mixture of fish oil and fish oil derived, choline based, phospholipid bound fatty acid mixture including polyunsaturated EPA and DHA in combination with astaxanthin and hyaluronate and optionally combined with glucosamine sulfate or its hydrochloride salt, chondroitin sulfate, hydrolyzed or unhydrolyzed collagen, elastin methylsulfonmethane, a gamma-linoleic acid or omega-3 fatty acid rich oil and a cyclooxgenase and/or lipoxygenase inhibitor for the treatment of symptoms related to joint pain or joint diseases including but not limited to osteoarthritis and rheumatoid arthritis.

In still another example, a composition is formulated in a therapeutic amount to treat and alleviate symptoms of osteoarthritis and/or rheumatoid arthritis, wherein the composition includes a mixture of fish oil and fish oil derived, choline based, phospholipid bound fatty acid mixture including polyunsaturated EPA and DHA in combination with astaxanthin and polymers of hyaluronic acid or sodium hyaluronate (hyaluronan) in an oral dosage form. This composition may include other active constituents as explained and identified above relative to the method and composition.

A method to treat and alleviate symptoms of osteoarthritis and/or rheumatoid arthritis in a patient is disclosed by administering a composition comprising a therapeutic amount of omega choline. In another example, the omega choline is administered with hyaluronic acid of varying molecular weights. In another example, therapeutic composition includes a mixture of fish oil and fish oil derived, choline based, phospholipid bound fatty acid mixture including polyunsaturated EPA and DHA admixed with hyaluronic acid of varying molecular weights and astaxanthin.

DETAILED DESCRIPTION OF THE PREFERRED EMBODIMENTS

The present invention will now be described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The composition includes EPA and DHA functionalized as EPA and DHA bound choline based phospholipids and acyltriglycerides derived from a mixture of fish oil and fish oil derived, choline based, phospholipid bound fatty acid mixture including polyunsaturated EPA and DHA astaxanthin, and in one non-limiting example, low molecular weight polymers of hyaluronic acid or sodium hyaluronate (hyaluronan) in an oral dosage form. In other examples, the hyaluronic acid has varying molecular weights.

As noted before, surprisingly the composition includes a pro-inflammatory low molecular weight Hyaluronic Acid (LMWtHA). Natural high molecular weight hyaluronic acid is the major hydrodynamic component of synovial fluid and importantly is known to be immuno-neutral to the innate immune system. It is nature's bone joint shock absorbent and lubricant. It has been found that there is excellent oral bioavailability of LMWtHA fragments specifically to connective tissue, which maximizes interaction with targeted cell receptors which may mediate the innate immune response in diseased joints. Therefore in a preferred composition containing a mixture of fish oil and fish oil derived, choline based, phospholipid bound fatty acid mixture including polyunsaturated EPA and DHA and astaxanthin two anti-inflammatory components and LMWtHA are thus combined with one highly inflammatory component. The scientific literature indicates that LMWtHA fragments in in vitro studies has been shown to exhibit potent pro-inflammatory behavior. It therefore remains unclear why a pro-inflammatory component would elicit a favorable overall response in inflamed joint tissues. It is believed that such pro-inflammatory LMWtHA fragments may promote site repair by simulation of the innate immune system repair mechanism and by simulating production of non-immunogenic high molecular weight HA bringing the joint back to homeostasis, however these are merely unproven theories. A great deal of work by leading immunologists is still attempting to unravel all the aspects of the complicated singling processes associated with the innate immune system. Studies using large animal models of osteoarthritis have shown that mild immunogenic Hyaluronic Acids with molecular weights within the range of $0.5\text{-}1.0 \times 10^6$ Da (Dalton) were generally more effective in reducing indices of synovial inflammation and restoring the rheological properties of SF (visco-induction) than non-immunogenic HA's with molecular weights $>2.3 \times 10^6$ Da. This treatment evolved from treating horses with sterile injections of such hyuronates.

Astaxanthin is a component of the instant invention in some examples. Related scientific literature indicates that in a lipopolysaccharide induced inflammatory rat model, astaxanthin at just 1 mg/kg in vitro and in vivo: (1) down regulates TNF-alpha production by 75%; (2) down regulates prostaglandin E-2 production (PGE-2) by 75%; (3) inhibits nitric oxide synthase (NOS) expression of nitric oxide by 58%; and (4) these effects on inflammatory markers were nearly as effective as prednisolone in this model. Such information suggests but does not prove that astaxanthin may be an effective standalone product for the reduction of OA and/or RH pain or other symptomology associated with OA and/or RH however high doses of astaxanthin are required to achieve such anti-inflammatory results to date.

In induced uveitis, astaxanthin also showed dose dependant ocular anti-inflammatory activity by suppression of NO, PGE-2 and TNF-Alpha by directly blocking NO synthase activity. Astaxanthin is also known to reduce C-Reactive Protein (C-RP) blood levels in viva. For example, in human subjects with high risk levels of C-RP three months of astaxanthin treatment resulted in 43% of patients serum C-RP levels to drop below the risk level. This may explain why C-RP levels dropped significantly in the referenced Deutsch study. Astaxanthin is so powerful that it has been shown to negate the pro-oxidant activity of Vioxx in in vitro experiments, a COX-2 inhibitor belonging to the NSAIDS drug class which is now known to cause cellular membrane lipid per-oxidation leading to heart attack and stroke and was thus removed from the US pharmaceutical market. Astaxanthin is absorbed in vitro by lens epithelial cells where it suppresses UVB induced lipid per-oxidative mediated cell damage at umol/L concentrations. In human trials astaxanthin at 4 mgs/day prevented post exercise joint fatigue following strenuous knee exercise when compared to untreated subjects. These results have been shown in:

1) Lee et al., Molecules and Cells, 16(1):97-105; 2003;
2) Ohgami et al., Investigative Ophthalmology and Visual Science 44(6):2694-2701, 2003;
3) Spiller et al., J. of the Amer. College of Nutrition, 21(5): October 2002; and
4) Fry et al., Univ. of Memphis Human Performance Laboratories, 2001 and 2004, Reports 1 & 2.

A preferred composition in one embodiment includes 300 mg of krill oil, 45 mg of low molecular weight HA, and 2 mg astaxanthin.

Astaxanthin has potent singlet oxygen quenching activity. Astaxanthin typically does not exhibit pro-oxidant activity unlike β-carotene, lutein, zeaxanthin and Vitamins A and E. Astaxanthin in some studies has been found to be about 50 times more powerful than Vitamin E, 11 times more powerful than β-carotene and three times more powerful than lutein in quenching of singlet oxygen. Astaxanthin is also well known for its ability to quench free radicals. Comparative studies have found astaxanthin to be 65 times more powerful than Vitamin C, 54 times more powerful than β-carotene, 47 times more powerful than lutein, and 14 times more powerful than Vitamin E in free radical quenching ability.

Studies have shown that HA binds to the surface of dendritic cells ("DC's") and stimulated T-cells. Blockade of the CD44-HA interaction leads to impaired T-Cell activation both in vitro and in vivo. Studies have also shown that in cancer cell lines, LMWtHA fragments specifically induce nitric oxide synthase, a pro-inflammatory cytokine, in dendritic cells. In DC's, NO expression caused dendritic cell apoptosis (cell death). DC's are essential T-cell activators which function by presenting antigens to T-cells, thus apoptosis of DC's may short circuit the adaptive immune system response. This effect was clearly CD44 dependent because pretreatment of DC's with anti-CD44 monoclonal antibodies blocked the NO mediated induction of DC apoptosis. It appears that low molecular weight HA fragments interrupt the normal course of the well known T-cell mediated adaptive immune system response. CD44 is a glycoprotein responsible in part for lymphocyte activation (also known as T-cell activation) and is known to specifically bind to HA. On the other hand, as previously discussed, low molecular weight HA fragments appear to up-regulate the innate immune response, particularly in chronic inflammatory conditions where the innate immune system may in some way be compromised.

Support for such teachings can be found in:
1) Mummert et al., J. of Immunol. 169, 4322-4331;
2) Termeer et al., Trends in Immunology, Vol. 24, March 2003;
3) Yang et al., Cancer Res. 62, 2583-2591; and
4) McKee et al., J. Biol. Chem. 272, 8013-8018.

Additional information can be found in the following references: Ghosh P. Guidolin D. Semin Arthritis Rheum., 2002 August; 32(1):10-37; and P. Rooney, M. Wang, P. Kumar and S. Kumar, Journal of Cell Science 105, 213-218 (1993).

The '372 parent application discusses the beneficial aspects of using krill oil in synergistic combination with other ingredients. It has been determined that a fish oil and fish oil derived, choline based, phospholipid bound fatty acid mixture including polyunsaturated EPA and DHA is also advantageous for the treatment of some joint disease states either alone or admixed with other ingredients. One commercially available example of a mixture of fish oil and fish oil derived, choline based, phospholipid bound fatty acid mixture including polyunsaturated EPA and DHA is Omega Choline 1520F as a phospholipid, omega-3 preparation, which is derived from natural fish oil and sold by Enzymotec Ltd. One example of such composition is described below:

Ingredients (g/100 g):

| Pure Marine Phospholipids | n.l.t. 15 |
|---|---|
| DHA* | n.l.t. 12 |
| EPA** | n.l.t. 7 |
| Omega-3 | n.l.t. 22 |
| Omega-6 | <3 |

*Docosahexaenoic acid
**Eicosapenteanoic acid

Analytical Data:

| Peroxide value (meq/Kg) | n.m.t. 5 |
|---|---|
| Loss on Drying (g/100 g) | n.m.t. 2 |

Physical Properties:

| Consistency | Viscous Liquid |
| --- | --- |

Astaxanthin has an excellent safety record. A study conducted by Stewart et al. 2008 obtained the following results:
Oral LD 50: 600 mg/kg (rats);
NOAEL: 465 mg/kg (rats); or
Serum Pharmacokinetics:
1) $T_{1/2}$: 16 hours;
2) $T_{max}$: 8 hours;
3) $C_{max}$: 65 µg/L.

At eight weeks of supplementation at 6 mg per day, there was no negative effect in healthy adults. Spiller et al. 2003.

In accordance with one non-limiting example, astaxanthin has two primary renewable sources, namely a 1% to 12% astaxanthin oleoresin extracted from the micro algae *Haematococcus pluvialis* or 1.5-2.5% beadlet derived from the same microalgae.

In accordance with a non-limiting example, the method treats and alleviates symptoms of osteoarthritis and/or rheumatoid arthritis in a patient by administering a therapeutic amount of a composition including a mixture of fish oil and fish oil derived, choline based, phospholipid bound fatty acid mixture including polyunsaturated EPA and DHA in combination with astaxanthin and pro-inflammatory low molecular weight polymers of hyaluronic acid or sodium hyaluronate (hyaluronan) in an oral dosage form. The mixture of fish oil and fish oil derived, choline based, phospholipid bound fatty acid mixture including polyunsaturated EPA and DHA in one example comprises Eicosapentaenoic (EPA) and Docosahexaenoic (DHA) fatty acids in the form of triacylglycerides and phospholipids, although not less than 1% EPA and 5% DHA has been found advantageous. In another example, the omega choline includes at least 15% EPA and 9% DHA, of which not less than 45% are in the form of phospholipids. The composition can be delivered advantageously for therapeutic results with 1-4000 mg of a mixture of fish oil and fish oil derived, choline based, phospholipid bound fatty acid mixture including polyunsaturated EPA and DHA delivered per daily dose. In another example, 0.1-20 mg astaxanthin are supplemented to the omega choline per daily dose.

It should be understood that an instant formulation can be used for the relief of joint discomfort that includes only a mixture of fish oil and fish oil derived, choline based, phospholipid bound fatty acid mixture including polyunsaturated EPA and DHA. It is possible to use a mixture of fish oil and fish oil derived, choline based, phospholipid bound fatty acid mixture including polyunsaturated EPA and DHA mixed with hyaluronic acid of varying molecular weights or a mixture of fish oil and fish oil derived, choline based, phospholipid bound fatty acid mixture including polyunsaturated EPA and DHA mixed with hyaluronic acid of varying molecular weights and astaxanthin. It should also be understood that an enriched version of a mixture of fish oil and fish oil derived, choline based, phospholipid bound fatty acid mixture including polyunsaturated EPA and DHA can be used wherein the fraction of added fish oil diluents has been decreased and the proportion of fish oil derived phospholipids has been increased. This can be accomplished by using supercritical CO2 and/or solvent extractions for selective removal of triacylglycerides from phospholipids. In one example, the mixture of fish oil and fish oil derived, choline based, phospholipid bound fatty acid mixture including polyunsaturated EPA and DHA comprises not less than 15 g/100 g of marine phospholipids, not less than 12 g/100 g of DHA, and not less than 7 g/100 g of EPA. In another example, the mixture of fish oil and fish oil derived, choline based, phospholipid bound fatty acid mixture including polyunsaturated EPA and DHA comprises not less than 22 g/100 g of omega-3 and less than 3 g/100 g of omega-6.

It should also be understood that although the hyaluronic acid has been described as having low molecular weight, the mixture of fish oil and fish oil derived, choline based, phospholipid bound fatty acid mixture including polyunsaturated EPA and DHA can be mixed with hyaluronic acid of varying molecular weights depending on circumstances of use.

The astaxanthin is preferably derived from *Haematococcus pluvialis* algae, *Pfaffia*, krill, or by synthetic routes, in the free diol, monoester or diester form at a daily dose of 0.5-8 mg. The polymers of hyaluronic acid or sodium hyaluronate (hyaluronan) can be derived from microbial fermentation or animal tissues. About 1-500 mg of hyaluronan can be delivered per daily dose and preferably between 10 and 70 mgs/dose. In another example, the hyaluronic acid is derived from a bio-fermentation process and has a molecular weight between 0.5 and 100 kilodaltons (kDa). In another example, the polymers of hyaluronic acid or sodium hyaluronate (hyaluronan) are derived from microbial fermentation or animal tissue and have molecular weights exceeding 100 KDa and preferably up to $10^6$ KDa.

The composition may also include a natural or synthetic cyclooxygenase-1 or -2 inhibitor comprising for example aspirin, acetaminophen, steroids, prednisone, or NSAIDs. The composition may also include a gamma-linoleic acid rich oil comprising Borage (*Borago officinalis* L.) or Safflower (*Carthamus tinctorius* L.), which delivers a metabolic precursor to $PGE_1$ synthesis.

The composition may also include an n-3 (omega-3) fatty acid rich oil derived from fish oil, algae oil, flax seed oil, chia seed oil or perilla seed oil and the n-3 fatty acid comprises alpha-linolenic, stearidonic, eicosapentaenoic or docosapentaenoic acid. Hydrolyzed or unhydrolyzed collagen and elastin derived from eggshell membranes can also be advantageously added. The composition may also include anti-inflammatory and/or natural joint health promoting compounds comprising at least one of preparations of green lipped mussel (*Perna canaliculus*), *Boswellia serrata*, turmeric (*Curcuma* Tonga), stinging nettle (*Urtica dioica*), Andrographis, Cat's claw (*Uncaria tomentosa*), bromelain, methylsulfonylmethane (MSM), chondroitin sulfate, glucosamine sulfate or its hydrochloride salt, s-adenosyl-methionine, proanthocyanidins, or flavonoids. The composition may include naturally-derived and synthetic antioxidants that are added to retard degradation of fatty acids such as tocopherols, tocotrienols, carnosic acid or Carnosol and/or astaxanthin.

Different compositions may use different ingredients in combination with the a mixture of fish oil and fish oil derived, choline based, phospholipid bound fatty acid mixture including polyunsaturated EPA and DHA, astaxanthin and hyaluronate and be combined with different ingredients and supplemental compositions for more specific purposes.

A pharmaceutically acceptable composition comprises a mixture of fish oil and fish oil derived, choline based, phospholipid bound fatty acid mixture including polyunsaturated EPA and DHA in combination with astaxanthin and hyaluronate optionally combined with one or more ingredients including but not limited to glucosamine sulfate, chondroitin sulfate, collagen, methylsulfonmethane, a gamma-linoleic acid or omega-3 fatty acid rich oil, a cyclooxgenase inhibitor or a lipoxygenase inhibitor for the treatment of symptoms related to joint diseases including but not limited to osteoarthritis and rheumatoid arthritis.

In yet another example, a dietary supplement acceptable composition comprises a mixture of fish oil and fish oil derived, choline based, phospholipid bound fatty acid mixture including polyunsaturated EPA and DHA in combination with astaxanthin and hyaluronate optionally combined one or more ingredients, including but not limited to, glucosamine sulfate, chondroitin sufate, collagen, methylsulfonmethane, a gamma-linoleic acid or omega-3 fatty acid rich oil a cyclooxgenase inhibitor or a lipoxygenase inhibitor for the treatment of symptoms related to joint diseases including but not limited to osteoarthritis and rheumatoid arthritis.

In yet another example, a medical food acceptable composition comprises a mixture of fish oil and fish oil derived, choline based, phospholipid bound fatty acid mixture including polyunsaturated EPA and DHA in combination with astaxanthin and hyaluronate and optionally combined with one or more ingredients including glucosamine sulfate, chondroitin sufate, collagen, methylsulfonmethane, a gamma-linoleic acid or omega-3 fatty acid rich oil, a cyclooxgenase inhibitor or a lipoxygenase inhibitor for the treatment of symptoms related to joint diseases including but not limited to osteoarthritis and rheumatoid arthritis.

In still another example, a composition is formulated in a therapeutic amount to treat and alleviate symptoms of osteoarthritis and/or rheumatoid arthritis, wherein the composition includes a mixture of fish oil and fish oil derived, choline based, phospholipid bound fatty acid mixture including polyunsaturated EPA and DHA in combination with astaxanthin and polymers of hyaluronic acid or sodium hyaluronate (hyaluronan) in an oral dosage form. This composition may include other active constituents as explained and identified above relative to the method and composition.

Osteoarthritis (OA) is the most prevalent form of arthritis. Osteoarthritis is a disease in which the cartilage that acts as a cushion between the bones in joints begins to wear away causing bone on bone joint swelling and joint pain. It is characterized by degeneration of articular cartilage along with a peri-articular bone response. It affects both sexes, mainly in the fourth and fifth decades of life. The knee joint is most commonly affected joint. At present the management is by pharmacological and non-pharmacological therapy. Corrective surgical therapy and or joint replacement therapy in some cases may not be possible.

Traditional treatments for Osteoarthritis involve the use of analgesics, non-steroidal anti-inflammatory drugs (NSAIDs) or cyclooxgenase-2 specific (COX-2) NSAIDs alone or in combination with other active analgesics including but not limited to opiods or steroids. Advances in recombinant protein synthesis also provide relief from the symptoms of OA and RH by the use of genetically engineered proteins with specific functionality. Steroids or high molecular weight hyaluronic acid injections have also been used with some success, however, these therapies have well known deleterious side effects.

Many of these treatments alone have shown limited effectiveness in clinical trials. To avoid the cardiac risks and gastrointestinal issues associated with traditional OA treatments (particularly with long term use), many patients have turned to complimentary and alternative medicines (CAMs) such as dietary supplements. Glucosamine and chondroitin alone or in combination, are widely marketed as dietary supplements to treat joint pain due to OA. A major clinical trial on glucosamine and chondroitin (The GAIT Study) failed to show any significant improvement in WOMAC scores over placebo except in the highest quartile of patients studied. Because of their limited effectiveness, the search for additional CAMs to treat OA continues (see for example Ruff et al., Eggshell membrane in the treatment of pain and stiffness from Osteoarthritis of the knee: a randomized, multicenter, double-blind, placebo-controlled clinical study, Clin. Rheumatol (2009) 28:907-914).

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method to treat and alleviate symptoms of joint pain in a patient by administering a therapeutic amount of a dietary supplement composition including a therapeutic amount of a fish or marine oil derived product containing at least Eicosapentaenoic (EPA) and Docosahexaenoic (DHA) fatty acids present in at least one of the triacylglyceride and phospholipid bound forms in combination with astaxanthin and pro-inflammatory low molecular weight microbial fermented sodium hyaluronate fragments having a molecular weight between 0.5 and 300 kilodaltons (kDa) in an oral dosage form to treat and alleviate symptoms of joint pain in a patient.

2. The method according to claim 1, wherein the fish or marine oil derived product contains at least EPA and DHA fatty acids present in at least one of the tracylglyceride and phospholipid bound forms derived from fish.

3. The method according to claim 1, wherein the fish or marine oil derived product containing at least EPA and DHA fatty acids present in at least one of triacylglyceride and phospholipid bound forms comprises not less than (n.l.t.) 15 g/100 g of fish or marine oil based phospholipids, n.l.t. 12 g/100 g of DHA, and n.l.t. 7 g/100 g EPA.

4. The method according to claim 1, wherein the fish or marine oil derived product containing at least EPA and DHA fatty acids present in at least one of the triacylglyceride and phospholipid bound forms comprises n.l.t. 22 g/100 g of Omega-3 and less than 3 g/100 g of Omega-6.

5. The method according to claim 1, wherein the fish or marine oil derived product containing at least EPA and DHA fatty acids present in at least one of the triacylglyceride and phospholipid bound forms includes at least 7% EPA and 12% DNA, of which not less than 15% are in the form of phospholipids.

6. The method according to claim 1, and wherein the phospholipid fraction of the mixture of fish or marine oil derived product is enriched in phospholipid content using supercritical solvent fractionation of the triacylglyceride fraction away from phospholipids to decrease triacylglyceride content and increase fish or marine oil derived phospholipid contents.

7. The method according to claim 1, comprising delivering 1-4000 mg of fish or marine oil derived phospholipid bound fatty acid mixture including polyunsaturated EPA and DHA per daily dose.

8. The method according to claim 1, comprising delivering 0.1-20 mg astaxanthin supplemented to the fish or marine oil derived phospholipid bound fatty acid mixture including polyunsaturated EPA and DHA per daily dose.

9. The method according to claim 1, wherein the astaxanthin is derived from *Haematococcus pluvialis* algae, *Pfaffia*, krill, or by synthetic routes, in the free diol, monoester or diester form.

10. The method according to claim 1, wherein the fish or marine oil derived product comprises a fish oil derived, choline based, phospholipid bound fatty acid mixture.

* * * * *

UNITED STATES PATENT AND TRADEMARK OFFICE
CERTIFICATE OF CORRECTION

PATENT NO. : 9,597,300 B2  
APPLICATION NO. : 14/700510  
DATED : March 21, 2017  
INVENTOR(S) : Minatelli et al.

Page 1 of 1

It is certified that error appears in the above-identified patent and that said Letters Patent is hereby corrected as shown below:

On the Title Page

Item (72) Inventors:  Delete:  
"John A. Minatelli, Mounta Dora, FL (US)"  
Substitute:  
-- John A. Minatelli, Mount Dora, FL (US) --

In the Claims

Column 10, Line 36:  Delete: "tracylglyceride"  
Substitute: -- triacylglyceride --

Column 10, Line 53:  Delete: "DNA"  
Substitute: -- DHA --

Signed and Sealed this  
Ninth Day of May, 2017

Michelle K. Lee  
*Director of the United States Patent and Trademark Office*